United States Patent
Donnelly et al.

(10) Patent No.: US 6,743,610 B2
(45) Date of Patent: Jun. 1, 2004

(54) METHOD TO PRODUCE SUCCINIC ACID FROM RAW HYDROLYSATES

(75) Inventors: Mark I. Donnelly, Warrenville, IL (US); Cynthia Y. Sanville-Millard, Plainfield, IL (US); Nhuan Phu Nghiem, Knoxville, TN (US)

(73) Assignee: The University of Chicago, Chicago, IL (US)

( * ) Notice: Subject to any disclaimer, the term of this patent is extended or adjusted under 35 U.S.C. 154(b) by 105 days.

(21) Appl. No.: 09/823,949

(22) Filed: Mar. 30, 2001

(65) Prior Publication Data

US 2003/0017559 A1 Jan. 23, 2003

(51) Int. Cl.⁷ .................................................. C12P 7/46
(52) U.S. Cl. ...................... 435/145; 435/41; 435/132; 435/134; 435/252.3
(58) Field of Search .................. 435/41, 132, 134, 435/145, 252.3

(56) References Cited

U.S. PATENT DOCUMENTS 5,573,931 A * 11/1996 Guettler et al. ............. 435/145
5,770,435 A    6/1998 Donnelly et al.
6,159,738 A    12/2000 Donnelly et al.

OTHER PUBLICATIONS

R. Chatterjee, "Mutation of ptsG Gene Results in Increased Production of Succinate in Fermentation of Glucose by Escherichia coli",*Applied and Environmental Microbiology* Jan. 2001, vol. 67, No. 1, pp148–154.

* cited by examiner

*Primary Examiner*—Ponnathapu Achutamurthy
*Assistant Examiner*—Christian L. Fronda
(74) *Attorney, Agent, or Firm*—Cherskov & Flaynik

(57) ABSTRACT

A method for producing succinic acid from industrial-grade hydrolysates is provided, comprising supplying an organism that contains mutations for the genes ptsG, pflB, and ldhA, allowing said organism to accumulate biomass, and allowing said organism to metabolize the hydrolysate. Also provided is a bacteria mutant characterized in that it produces succinic acid from substrate contained in industrial-grade hydrolysate in a ratio of between 0.6:1 and 1.3:1 succinic acid to substrate.

17 Claims, 3 Drawing Sheets

METHOD TO PRODUCE SUCCINIC ACID FROM RAW HYDROLYSATES

CONTRACTUAL ORIGIN OF THE INVENTION

The United States Government has rights in this invention pursuant to Contract Number W-31-109-ENG-38 between the U.S. Department of Energy and the University of Chicago representing Argonne National Laboratory.

BACKGROUND OF THE INVENTION

1. Field of the Invention

This invention relates to a fermentation method to produce succinic acid, and more particularly this invention relates to a method for creating a bacterial strain capable of utilizing a myriad of sugars to produce succinic acid as a major fermentation product.

2. Background of the Invention

Carboxylic acids hold promise as potential precursors for numerous chemicals. For example, succinic acid can serve as a feedstock for such plastic precursors as 1,4 butanediol (BDO) tetrahydrofuran, and gamma-butyroactone. New products derived from succinic acid are under development, with the most notable of these being polyester which is made by linking succinic acid and BDO. Generally, esters of succinic acid have the potential of being new, "green" solvents that can supplant more harmful solvents. In total, succinic acid could serve as a precursor for millions of pounds of chemicals annually at a total market value of over $1 billion. Along with succinic acid, other 4-carbon dicarboxylic acids, such as malic acid, and fumaric acid also have feedstock potential.

The production of these carboxylic acids from renewable feedstocks (in this case through fermentation processes) is an avenue to supplant the more energy intensive methods of deriving such acids from nonrenewable sources. Succinate is an intermediate for anaerobic fermentations by propionate-producing bacteria but those processes result in low yields and concentrations.

Anaerobic rumen bacteria, such as *Bacteroides ruminicola* and *Bacteroides amylophilus* also produce succinate. However, rumen organisms are characteristically unstable in fermentation processes.

It has been long been known that a mixture of acids are produced from *E. coli* fermentation, as elaborated in Stokes, J. L. 1949 "Fermentation of glucose by suspensions of *Escherichia coli*" J. Bacteriol. 57:147–158. However, for each mole of glucose fermented, only 1.2 moles of formic acid, 0.1–0.2 moles of lactic acid, and 0.3–0.4 moles of succinic acid are produced. As such, efforts to produce carboxylic acids fermentatively have resulted in relatively large amounts of growth substrates, such as glucose, not being converted to the desired product.

Some bacteria, such as *A. succiniciproducens*, utilized in fermentation processes as outlined in U.S. Pat. No. 5,143,834 to Glassner et al., naturally produce succinic acid in moderate liters up to only about 35–40 grams per liter (g/L). The *A. succiniciproducens* host strain has been shown to be not highly osmotolerant in that it does not tolerate high concentrations of salts and is further inhibited by moderate concentrations of product. Lastly, *A. succiniciproducens* presents handling in that as an obligate anaerobe, procedures using the organism must be done in the absence of oxygen. Also, medium preparation for the inoculum requires the addition of tryptophan.

Previous efforts by the inventors to produce succinic acid has resulted in the isolation and utilization of a mutant bacterium. The mutant, available as ATCC accession number 202021, is the subject of U.S. Pat. Reissue application Ser. No. 09/429,693. Reissue application Ser. No. 09/429,693, incorporated herein by reference, teaches a succinic acid-producing bacterial stain (AFP 111) which spontaneously mutates from its precursor. The mutant is able to grow fermentatively on glucose to produce succinic acid in high yields, while its precursors are unable to do so. However, an obvious drawback to utilizing this method of succinic acid production is its limitation to a single mutant.

Other efforts (U.S. Pat. No. 6,159,738) by the inventors have resulted in a method for constructing bacterial strains having increased succinic acid production. The method teaches that alteration of the phosphotransferase gene of *E. coli* causes the bacteria to produce more succinic acid. A drawback to this method is its limitation to a single alteration.

A need exists in the art for a method for producing succinic acid fermentatively, whereby the method is not relegated to a single mutant or gene. The method should be enabled by any organism having a particular, and easily determined, genotype. The method should be able to be performed in relatively inert conditions using robust organisms (i.e., those having high feed back inhibition thresholds), and also so as to obviate the need for sophisticated environmental control measures. The method should produce superior results utilizing mixtures of sugars derived from hydrolysis of lignocellulosic materials, inasmuch as these substrates offer a cheaper source of sugars, and as such, their use could reduce production costs for succinic acid.

SUMMARY OF THE INVENTION

It is an object of the present invention to provide a method of producing succinic acid that overcomes many of the disadvantages of the prior art.

It is another object of the present invention to provide a fermentation process that produces high yields of succinic acid. A feature of the invention is the utilization of bacterial genomes containing a plurality of mutant genes to enable the method. An advantage of the invention is that bacteria can be readily manipulated to produce the plurality of mutants. Alternatively, bacteria already containing the plurality of mutations can be utilized without further manipulation.

Still another object of the present invention is to provide a process for manipulating bacteria to produce large amounts of succinic acid. A feature of the invention is the disruption of the normal regulation of sugar metabolism in the bacteria. An advantage of the invention is the ability to manipulate a variety of bacteria to facilitate relatively high product-to-growth substrate ratios (i.e., at or above 1:1) in fermentation processes for producing succinic acid. Another advantage of the invention is the ability to utilize bacteria which become glucose metabolisers and non-glucose metabolisers.

Yet another object of the present invention is to produce succinic acid fermentatively. A feature of the invention is the utilization of bacteria containing altered phosphotransferase (pts) systems, pyruvate formate lyase (pfl) systems, and lactate dehydrogenase (ldh) systems. An advantage of the invention is that the bacteria can be derived from many genera which use these enzyme systems for sugar fermentation.

Briefly a method of producing succinic acid from industrial-grade hydrolysates is provided, comprising: supplying an organism that contains mutations for the genes ptsG, pflB, and ldhA; allowing said organism to accumulate biomass; and allowing said organism to metabolize the hydrolysate.

Also provided is a bacteria mutant characterized in that it produces succinic acid from substrate contained in industrial-grade hydrolysate in a ratio of between 0.6:1 and 1.3:1 succinic acid to substrate (e.g., between 0.6 and 1.3 grams succinic acid per gram of total sugar consumed).

BRIEF DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

The inventors have developed a method for fermentatively producing high yields of succinic acid. The method exploits altered catabolite repression mechanisms of selected organisms so as to allow the organisms to produce succinic acid using mixtures of glucose and non-glucose feedstocks.

The resulting mutants and protocols result in a succinate to feedstock ratio of up to 1.3:1, and typically 0.9:1. Succinate accumulations of between 60 g/L and 75 g/L are achieved. Typical protocol durations are more than 70 hours, and usually between 120 and 170 hours. For example yields of 70 g/L are obtained after 160 hours. The process is viable at from between approximately 25° C. and 45° C., with a preferable range of approximately 30 to 39° C. A pH of between 5 and 9 is suitable, with a more preferable range of approximately 6.1 and 7.2.

The invented mutants are especially viable components of the fermentative protocol inasmuch as they have increased tolerance to fermentative products. For example, concentrations of 72 g/L for succinate, 22 g/L for acetate, 14 g/L for ethanol, and 8 g/L for lactate are achievable without inducing feedback inhibition.

Feedstock Detail

A salient feature of the invented method and mutant is the direct utilization of industrial feedstocks. A myriad of feedstocks can be utilized, including, but not limited to light steep water, lignocellulosic hydrolysate produced by various methods of hydrolysis, corn-derived sugar solutions (such as corn steep liquor), lactose from whey, and other industrial-grade sugars. For example, lignocellulosic hydrolysate produced by concentrated acid hydrolysis, or dilut acid hydrolysis, enzyme hydrolysis or hydrolysates produced by a combination of these processes are all suitable. Corn-derived sugar solutions are also suitable.

Figure 2:
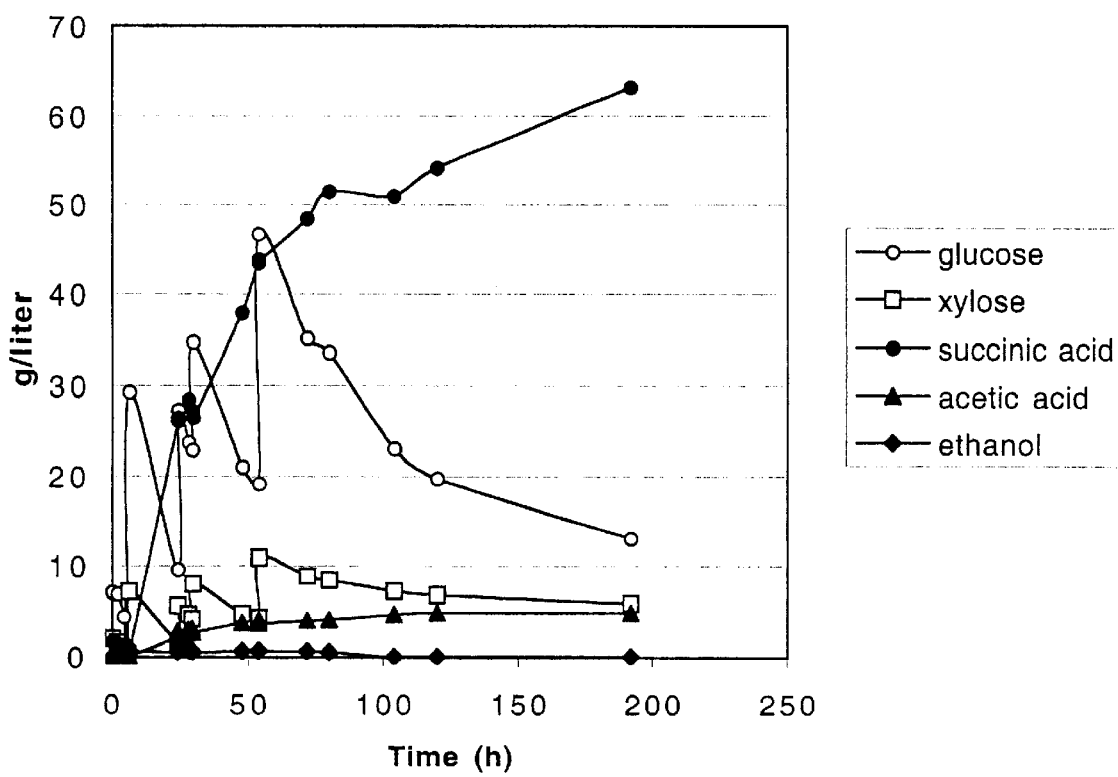
FIG. 2 is a graph depicting fermentation of industrial hydrolysate via a triple mutant organism, in accordance with features of the present invention.

Industrial feedstocks generally are mixtures of glucose and other sugars, the most common non-glucose sugar being xylose. FIG. 2 depicts the utilization of glucose and xylose by one of the invented mutants.

In light of the foregoing, any feedstocks containing glucose and/or nonglucose sugars are suitable. As such, feedstocks containing glucose, sorbitol, xylose, arabinose, mannose, lactose, glucuronic acid, galactose, fructose, and combinations thereof are appropriate.

Organism Detail

The invented method utilizes organisms containing alterations in the catabolite repression system of the organisms. These organisms contain an inoperative phosphotransferase system, an inoperative pyruvate formate lyase system, and an inoperative lactate dehydrogenase system. Specifically, the inventors have found that when alterations exist to the phosphotransferase (pts) system, pyruvate formate lyase (pfl) system, and lactate dehydrogenase (ldh) system of bacteria, these bacteria are suitable for use in the invented succinic acid producing process. pflAB and ldhA, are the genes encoding pyruvate:formate lyase and the fermentative lactate dehydrogenase, respectively.

NZN 111 is unable to ferment glucose due to inactivation of the genes encoding pyruvate:formate lyase and the fermentative lactate dehydrogenase. A mutation of the ptsG gene restores the ability of NZN 111 to grow fermentatively on glucose. When a null mutation of the ptsG gene is introduced into various strains of E. coli not blocked in the ability to ferment glucose, the resulting strains also produce more succinate.

The mapping results indicate that the ptsG allele lies between 24.6 and 25.5 mm on the E. coli chromosome. The ptsG gene lies at 25.0 mm. Its product, protein EIICB$^{glc}$, is the glucose-specific permease of the PTS.

E. coli normally carries out mixed-acid fermentation of glucose to give primarily acetate, formate, and ethanol, all of which are derived from pyruvate in a series of reactions initiated by pyruvate:formate lyase. Succinate, derived via carboxylation and subsequent reduction of PEP, is a minor product. In certain mutants, PEP derived from glucose is converted via the reductive arm of the tricarboxylic acid cycle to succinate. E. coil possesses a latent ability to carry out glucose fermentation to succinate when the genes encoding pyruvate:formate lyase (pflB), the fermentative lactate dehydrogenase (ldhA), and EIICB$^{glc}$ (ptsG) are inactivated.

Thus, the only limitation on the type of organism utilized in the invented fermentative process is that the organism originally must have these systems. An organism naturally containing alterations in these systems (i.e., spontaneous mutants), or organisms which are specifically altered, can be utilized.

In instances where the bacteria are altered, fermentative bacteria having no or low succinic acid product yields (i.e., less than 0.5 moles per one mole of fed growth substrate) are converted to bacteria having high succinic acid product yields (i.e., greater than or equal to 1 mole of succinic acid per one more of fed growth substrate).

Any bacterium able to make any succinic acid fermentatively are particularly suitable transduction candidates, including but not limited to gram-negative and gram-positive fermentative bacteria. Preferably, suitable strains include but are not limited to E.coli, Klebsiella, Erwinia, and Lactobacillus.

Organisms to be altered to include the three knockouts are modified by serial transduction using bacteriophage P1. Standard P1 transduction protocols were utilized, an exemplary protocol disclosed in J. H. Miller, ed. *Experiments in Molecular Genetics* 1972 (Cold Spring Harbor Laboratory, Cold Spring Harbor, N.Y.), and incorporated herein by reference.

In one instance, a nonproprietary strain C600 (ATCC Accession Number 23724) is modified to contain the three mutations. The resulting mutant is named AFP 184, (AFP= Alternative Feedstock Program) having ATCC Accession Number 202021. In this instance, C600 contains intact genes for all three systems. AFP 184 was the pfl deletion, ldh knockout, and the different mutant form of ptsG deliberately inserted into C600 to take advantage of that strain's strong growth characteristics and its ability to use xylose. (W1485 derivatives do not have these advantages.) AFP 415 differs from AFP 184 only in having the knockout of ptsG. It performs similarly to AFP 184.

The Miller paper, mentioned supra, provides protocol for the aforementioned C600 manipulation.

Surprisingly and unexpectedly, the inventors found that the metabolism rate and titer for C600 derivatives (e.g., the AFP 184 and AFP 415) are superior to the W1485 derivatives disclosed in U.S. Pat. Nos. 5,770,435 (now Reissue application Ser. No. 09/429,693) and U.S. Pat. No. 6,159,738.

Table 1 provides a comparison of succinic acid production by C600 derivatives and W1485 derivatives. It is noteworthy that while the W1485 derivatives utilized fairly refined feedstocks, the C600 derivatives still provided higher values with industrial grade hydrolysates.

A mutation containing all three knockouts also can be generated using a bacterium already containing one or two of the genetic anomalies, and then inducing the remainder knockout(s). In this instance, a viable starting organism is W1485, ATCC Accession Number 12435. AFP 400 is a deliberately-made triple knockout. It contains the pfl deletion by August Bock, and inserted into W1485 by David Clark of the University of Illinois to produce FMJ123. FMJ123 is produced pursuant to the protocol found in P. K. Bunch et al. (1997) *Microbiology* 143, 187–195, and incorporated herein by reference. AFP 400 also contains the ldhA knockout, also made by Clark and inserted into FMJ123 to produce DC1327. DC1327 is produced pursuant to the protocol found in Chatterjee et al, Appl. *Environ. Microbiol.* 67, pp148–154, and incorporated by reference. AFP 400 contains the ptsG knockout, as described in the Chafterjee reference.

TABLE 1

Comparison of Succinic Acid Production by Different Lineages Of *E. Coli*

| Strain | Max Concentration | Max Productivity | Yield (g/g glucose) |
| --- | --- | --- | --- |
| AFP 111 | 51 g/L | 0.87 g/Lh | 0.70 |
| AFP 184 | 72 g/L | 1.00 g/Lh | 1.00 |

A triple knockout AFP404 was also constructed by introduction of three knock-outs into strain C600. AFP404 is identical to AFP184 but has a knockout of ptsG rather than a point mutation of the gene. It also produces succinic acid in a yield of approximately 1 mol/mol glucose.

A protocol for development of the triple mutation from the wild strain also is found in R. Chatterjee et al. Typical antibiotic markers indicating presence of each of the knockouts include, but are not limited to, Cam, Tet, and Kan. New *E. coli* strains, AFP 400, and AFP 404 containing the knockouts and the antibiotic markers were thus generated. That protocol follows:

Construction and Introduction of an Insertionally Inactivated ptsG Gene

The native ptsG gene of *E. coli* was cloned by PCR from genomic DNA prepared from W1485 using primers targeting the N- and C-termini of the protein with no additional genomic sequences amplified. The gene was cloned in the vector pFJ118EH to give pJFptsG. The gene was disrupted by insertion of the kanamycin resistance cassette of pUC-4K (Pharmacia), excised with EcoRl, into the Mfel site of the ptsG gene in pJFptsG to give the plasmid pTSGK. Because NZN 111 already includes a kanamycin resistance marker, an equivalent stain was constructed by transducing Tn10-inactivated ldhA gene from stain SE1752 into FMJ123. The resulting strain, DC1327, was indistinguishable in its physiology from NZN 111. The disrupted ptsG gene was transferred in DC1327 by transforming the cells with pTSGK, growing the cells for approximately 30 generations in the presence of kanamycin and absence of ampicillin, then plating the culture on LB plates containing glucose and incubating anaerobically. Colonies that were able to grow fermentatively were purified and screened for their sensitivity to the two antibiotics.

Strain AFP400 was isolated as a stable kanamycin resistant, ampicillin sensitive strain that fermented glucose to succinate, acetate, and ethanol. Proper integration of the disrupted ptsG gene was confirmed by PCR. The disrupted gene was amplified from AFP400 DNA using primers that matched flanking sequences approximately 110 base pairs outside the coding region of the gene. These sequences were not present in the integration vector. The resulting product was 3.0 kb in size, as predicted from the known sequence ptsG, its flanking regions, and the Kanamycin insert. The product was digested with Clal (site in the kanamycin cassette) and Agel (site in ptsG), and generated the fragments expected for insertion of the cassette into the Mfel site of ptsG (1.95 and 1.05 kb for Clal, and 2.3 and 0.7 kb for Agel).

Yet another strain containing the three knock outs, AFP 404, is also derived from C600, a near wild-type *E. coli* K12 strain, using the same protocol above.

Location of the knockouts are already known from the inventor's previous research (U.S. Pat. No. 6,159,738, and Chatterjee et al.) discussed supra. The knockouts are introduced by putting a copy of the knock-out gene, having a resistance marker, into the cells. Homologous recombination is allowed to occur, as facilitated by host enzymes. The chromosome containing the marker is then selected. The ptsG knockout was introduced this way. Proof of its insertion, via PCR, is detailed in Chatterjee, et al., previously incorporated by reference.

Growth Detail

Figure 1:
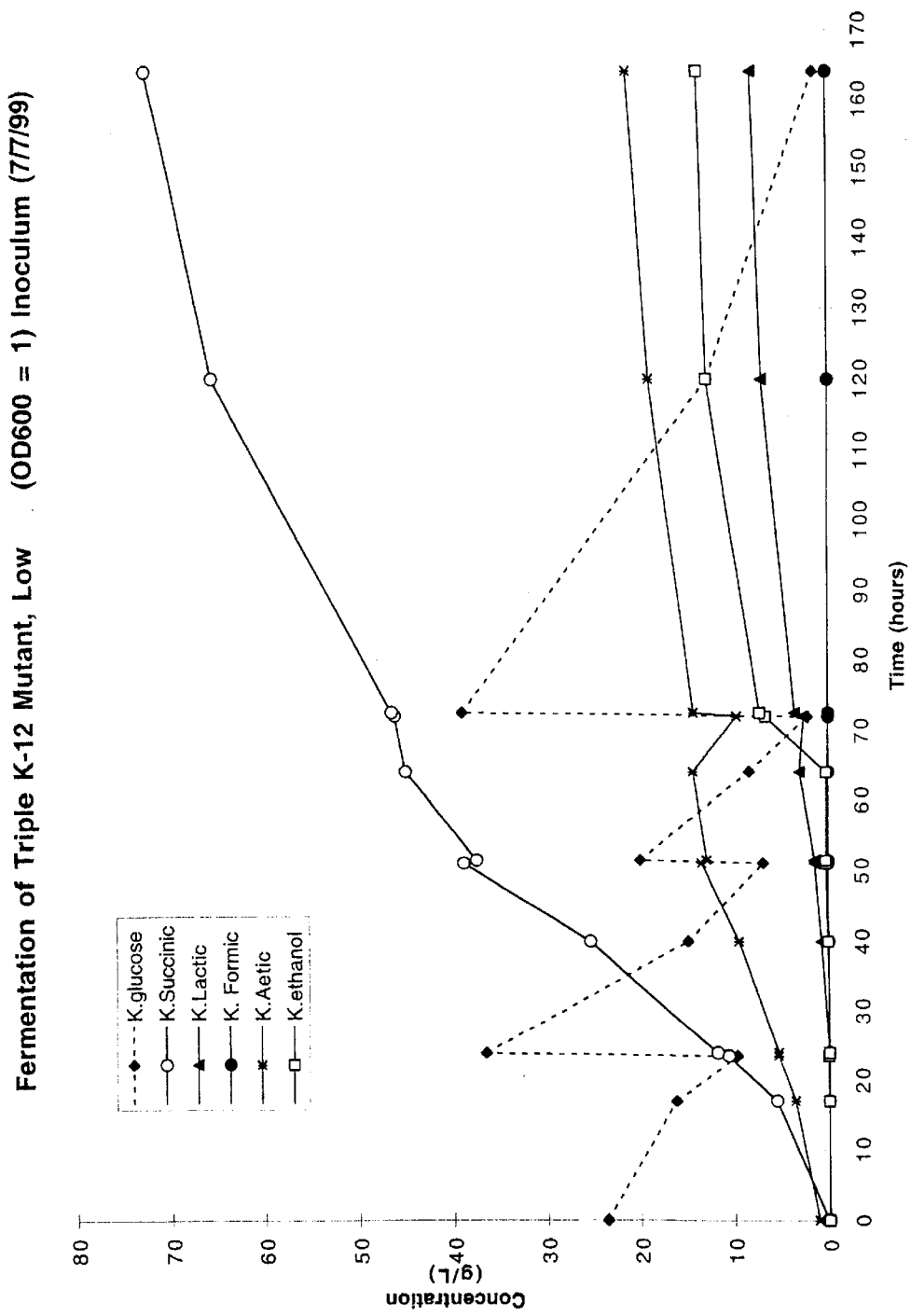
FIG. 1 is a graph depicting an enhanced production of succinic acid after transformation of a bacteria with a mutant gene, in accordance with features of the present invention.

The triple mutant organisms produced by the inventors are not obligate anaerobes. As such, initial accumulation of biomass can occur aerobically, after which fermentative conditions are established. The advantages of this two-stage process (i.e., aerobic-then anaerobic) protocol are illustrated in FIG. 2 wherein the rate of production of succinic acid is much larger compared to the single-stage anaerobic protocol growth curve of FIG. 1.

Generally, when the biomass reaches a point of the equivalent of approximately $10^8$ to $10^{11}$ cells per milliliter (or approximately 2 to 5 gram dry cell weight per liter), the fermenter is made anaerobic. In the laboratory, this concentration point was reached after approximately six hours.

In industrial protocols, a fermenter is charged with light steep water plus lignocellulosic hydrolyste. Antibiotics were included as necessary at the following concentrations: 100 $\mu$g of carbenicillin per ml, 30 $\mu$g of kanamycin per ml, 10 $\mu$g of tetracycline per ml, and 30 $\mu$g of chloramphenicol per ml. Rich broth contained (per liter), 10 g of tryptone, 5 g of NaCl, and 1 g of yeast extract. Solid media for plates contained 1.5 percent (wt/vol) Difco Bacto-Agar. Minimal medium E was prepared as described in Vogel, H. J. 1956 *Acetylornithinase in E. coli*, . Biol. Chem. 218:97–103, and incorporated herein by reference.

Laboratory conditions for the fermentation were as follows:

Fermentative growth was performed in sealed serum tubes containing 10 ml of LB medium, supplemented with 0.5 g of $MgCO_3$ (added in order to maintain the pH of the medium during fermentation), antibiotics, and approximately 10 g/L of glucose. A myriad of growth substrates can be utilized, including but not limited to sugars, sugar alcohols, sugar acids and combinations thereof. The following sugars were tested in place of glucose at a concentration of 5 g/L in anaerobic growth: trehalose, mannose, fructose, sorbitol, and glucuronic acid.

Innocula for the anaerobic liquid cultures were prepared by growing the strains aerobically overnight in LB medium supplemented with antibiotic. A sample of the overnight culture was diluted 100-fold in fresh media and allowed to grow aerobically to an $A_{600}$ of approximately 1; the anaerobic growth media was inoculated with 1 ml of the inocula.

Samples were removed anoxically from the sealed tubes at appropriate times for analysis of levels of glucose (or alternate sugar substrates) remaining and fermentation products formed. For anaerobic growth on solid media, agar plates were incubated at 37 C in an anaerobic jar under an $H_2$—$CO_2$ atmosphere generated by use of a Gas-Pak.

A plate assay for β-galactosidase activity was used to test for the presence of normal catabolite repression in strains. LB or Medium E-agar are two of several mediums which can be utilized. Medium E-agar is a minimum-nutrient medium commonly used, and discussed in Vogel, H. J., 1956 *Acetylornithase in E. coli*, J. Bio/Chem 218:97–103 and incorporated herein by reference. In exemplary protocols, LB or Medium E-agar is supplemented with 4 g/L of glucose, 4 g/L of lactose, 3 mg/L of 5-bromo-4-chloro-3-indolyl-β-D-galactoside (X-gal), and antibiotics. These media are hereinafter referred to as X-gal/glucose agar. The formation of blue colonies indicated expression of β-galactosidase in the presence of glucose due to the absence of normal catabolite repression. Conversely, the formation of white colonies indicated that normal catabolite repression existed, and therefore no enzyme was present to cleave the disaccharide lactose.

The inventors also have devised a method for utilizing the mutant in a continuous process. Repetitive experiments were conducted in which after the culture had produced approximately 50 g/L succinic acid, one milliliter of the mixture was added to a fresh enclosure containing LB media, glucose and $MgCO_3$. This new innoculum continued to produce succinic acid effectively. This process was repeated 3–4 times, in each case resulting in efficient production of succinic acid.

EXAMPLE 1

Succinic Acid Production Utilizing Industrial Hydrolysate

AFP 184 was placed in a fermenter with true hydrolysate, from rice straw. An exemplary hydrolysate is that commercially prepared and made available from Arkenol Inc., of Mission Viejo, Calif., via its concentrated acid hydrolysis process. The rice straw medium contains approximately 600 g/L glucose and 169 g/L xylose as the two main sugar components, plus minor quantities of other sugars. The experimental data are found in Table 2 and in FIG. 2.

The following is a protocol of the AFP 184-based fermentation process:

The fermentation medium contained the following components: Difco yeast extract 5 g/L, tryptone 10 g/L, (NH4)2SO4 2 g/L, MgSO4—7H2O 0.2 g/L, NaCl 10 g/L, K2HPO4 7 g/L, KH2PO4 3 g/L, Arkenol's hydrolysate 16.5 mL/L, and kanamycin 30 mg/L. The industrial hydrolysate contained 607 g/L glucose and 169 g/L xylose as the two main sugar components plus minor quantities of other sugars. The medium with all of the components except the antibiotic was autoclaved at 121° C. for 20 minutes. Kanamycin then was added upon cooling. This fermentation medium was used for both the inoculum flasks and the one-liter fermenter. For the inoculum, 50 mL medium was placed in a 250-mL flask and inoculated with 0.2 mL of the AFP184 stock culture which was maintained in 30% glycerol and at −70° C. The flask was incubated in a incubator shaker at 37° C. and 250 rpm overnight (about 16 hours). The entire flask contents then were used to inoculate the fermenter which was maintained at 37° C. The medium in the fermenter was aerated to allow fast growth of the organism. After six hours when the required cell mass was achieved, the following actions were taken: 1. Air was turned off to exert anaerobic conditions, which would initiate production of succinic acid; 2. Carbon dioxide gas was sparged into the medium at a rate of 0.03 mL per minute; and 3. A feed solution which contained the Arkenol's hydrolysate diluted with deionized water to a concentration of 500 g/L of total glucose plus xylose was added to the fermenter to achieve a total sugar concentration of 50 g/L in the fermentation medium. During the course of the experiment, when the sugar concentration in the fermnetr was low, more feed was added to provide sufficient substrates for succinic acid production. As the cells produced succinic acid the pH dropped. It was maintained at pH 6.5 by addition of a 1.5 M $Na_2CO_3$ solution through the action of an automatic pH controller. Samples were taken at intervals and analyzed for optical density, glucose, xylose, succinic acid, acetic acid, lactic acid, and ethanol.

TABLE 2

Production of Succinic Acid, Acetic Acid and Ethanol from Arkenol With a Mutant Containing ptsG, ldh, and pfl Anomalies

| Time | glucose | xylose | succinic acid | acetic acid | ethanol |
|---|---|---|---|---|---|
| 0 | 7.04 | 1.94 | 0 | 0 | 1.60 |
| 2 | 6.85 | 1.53 | 0 | 0.41 | 1.35 |
| 4.2 | 4.41 | 0 | 0 | 0.85 | 1.13 |
| 6 | 0 | 0 | 0 | 0.55 | 1.04 |
| 6.05 | 29.27 | 7.17 | 0 | 0 | 0.68 |
| 24 | 9.56 | 1.69 | 26.12 | 2.24 | 0.49 |
| 24.05 | 27.25 | 5.60 | 26.39 | 2.82 | 0.72 |
| 28.1 | 23.7 | 14.69 | 28.42 | 2.98 | 0.71 |
| 29.5 | 22.8 | 14.17 | 27.20 | 3.04 | 0.67 |
| 29.55 | 34.77 | 7.95 | 26.41 | 2.63 | 0.52 |
| 48 | 20.98 | 4.72 | 37.98 | 3.71 | 0.62 |
| 54 | 19.13 | 4.30 | 43.82 | 4.10 | 0.71 |
| 54.05 | 46.73 | 10.85 | 43.51 | 3.69 | 0.59 |
| 72 | 35.14 | 8.85 | 48.52 | 4.01 | 0.63 |
| 80 | 33.60 | 8.45 | 51.44 | 4.10 | 0.50 |
| 104.25 | 23.02 | 7.20 | 50.99 | 4.64 | 0 |
| 120 | 19.73 | 6.77 | 54.12 | 4.83 | 0 |
| 192 | 13.04 | 5.87 | 63.21 | 4.88 | 0 |

EXAMPLE 2

Succinic Acid Production From Synthetic Sugar Mixture

A fermentation protocol was developed utilizing AFP 184 in combination with a synthetic sugar feedstock. As can be noted on FIG. 3, succinate production was rapid up to 80 hours, and plataued somewhat before reaching a final high of 60 g/L after approximately 140 hours.

The fermentation medium contained the following components: Difco yeast extract 5 g/L, tryptone 10 g/L, (NH4)2SO4 2 g/L, MgSO4—7H2O 0.2 g/L, NaCl 10 g/L, K2HPO4 7 g/L, KH2PO4 3 g/L, glucose 7.6 g/L, xylose 1.85 g/L, and kanamycin 30 mg/L. The medium with all of the components except the antibiotic was autoclaved at 121° C. for 20 minutes. Kanamycin then was added upon cooling. This fermentation medium was used for both the inoculum flasks and the one-liter fermenter. For the inoculum, 50 mL medium was placed in a 250-mL flask and inoculated with 0.2 mL of the AFP184 stock culture which was maintained in 30% glycerol and at −70° C. The flask was incubated in a incubator shaker at 37° C. and 250 rpm overnight (about 16 hours). The entire flask contents then were used to inoculate the fermenter which was maintained at 37° C.

The medium in the fermenter was aerated to allow fast growth of the organism. After six hours when the required cell mass was achieved, the following actions were taken:

1. Air was turned off to exert anaerobic conditions, which would initiate production of succinic acid;
2. Carbon dioxide gas was sparged into the medium at a rate of 0.03 mL per minute; and
3. A feed solution which contained 400 g/L glucose and 84 g/L xylose was added to the fermenter to achieve a total sugar concentration of 50 g/L in the fermentation medium.

During the course of the experiment, when the sugar concentration in the fermenter was low, more feed was added to provide sufficient substrates for succinic acid production. As the cells produced succinic acid, the pH dropped. It was maintained at pH 6.5 by addition of a 1.5 M Na2CO3 solution through the action of an automatic pH controller. Samples were taken at intervals and analyzed for optical density, glucose, xylose, succinic acid, acetic acid, lactic acid, and ethanol.

Figure 3:
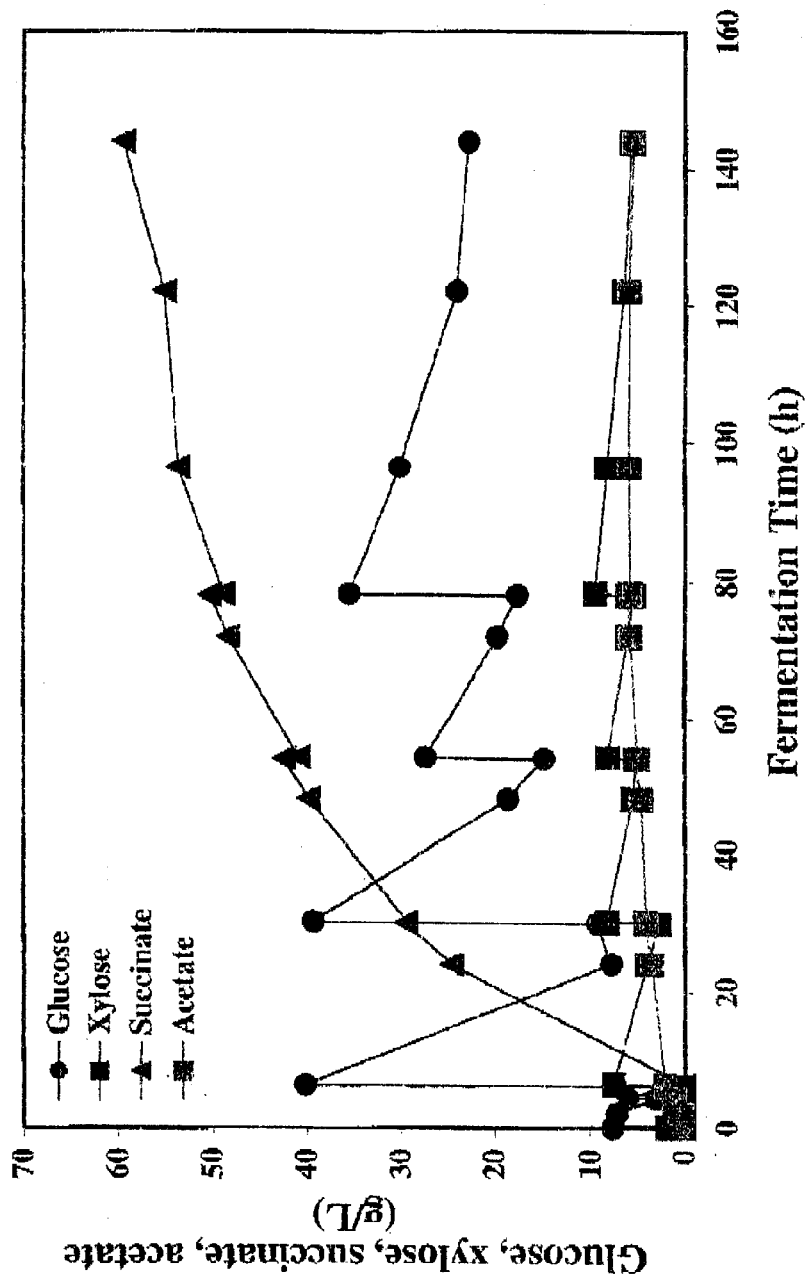
FIG. 3 is a graph depicting fermentation of synthetic sugar via a triple mutant organism, in accordance with features of the present invention.

Table 3, infra, and FIG. 3 illustrate the succinic acid production resulting from the utilization of the synthetic sugar mixture.

As can be noted in a comparison between Example 1 and Example 2, succinate production of the mutant was equivalent (see time points 120 and 122 of Table 2 and 3, respectively) when industrial hydrolysate was used versus when the synthetic feedstock was used. This result illustrates the robust character of the invented protocol in that any toxic materials inherent with industrial grade hydrolysates did not degrade the yield.

TABLE 3

Succinic Acid Production in a fermentation protocol utilizing Synthetic Sugar

| Time | Glucose | Xylose | Succinate | Acetate |
| --- | --- | --- | --- | --- |
| 0 | 7.65 | 1.85 | 0 | 0 |
| 2 | 7.19 | 1.03 | 0 | 0.32 |
| 4.2 | 3.15 | 0 | 0 | 1.1 |
| 4.45 | 6.03 | 0.84 | 0 | 1.1 |
| 6 | 1.04 | 0 | 0 | 2.02 |
| 6.25 | 40.2 | 7.57 | 0 | 2.02 |
| 24 | 7.76 | 3.92 | 24.55 | 3.43 |
| 30 | 9.18 | 2.63 | 29.34 | 4.11 |
| 30.25 | 39.3 | 8.2 | 29.34 | 4.11 |
| 48 | 18.6 | 5.5 | 39.8 | 4.6 |
| 54 | 14.8 | 4.95 | 42.33 | 5.26 |

TABLE 3-continued

Succinic Acid Production in a fermentation protocol utilizing Synthetic Sugar

| Time | Glucose | Xylose | Succinate | Acetate |
| --- | --- | --- | --- | --- |
| 54.25 | 27.4 | 8.1 | 40.77 | 4.9 |
| 72 | 19.7 | 6.04 | 48.33 | 5.76 |
| 78 | 17.6 | 5.42 | 50.27 | 6 |
| 78.25 | 35.5 | 9.49 | 48.87 | 5.75 |
| 96.5 | 30.2 | 8.25 | 53.62 | 5.87 |
| 122 | 24.1 | 6.48 | 55.1 | 5.87 |
| 144 | 22.8 | 5.67 | 59.35 | 5.43 |

While the invention has been described with reference to details of the illustrated embodiment, these details are not intended to limited the scope of the invention as defined in the appended claims.

The embodiment of the invention in which an exclusive property or privilege is claimed is defined as follows:

1. A method of producing succinic acid from plant hydrolysates comprising:
    a) supplying an organism, selected from the group consisting of AFP 184, AFP 400 and AFP 404;
    b) contacting said organism with hydrolysates said;
    c) allowing said organism to metabolize said hydrolysates; and
    d) isolating and recovering the succinic acid from the organism.

2. The method as recited in claim 1 wherein the organism accumulates to between approximately $10^8$ to $10^{11}$ cells per milliliter.

3. The method as recited in claim 1 wherein the plant hydrolysate is lignocellulosic hydrolysate, or corn-derived sugar solution.

4. The method as recited in claim 1 wherein the temperature is selected from between approximately 25° C. and 45° C.

5. The method as recited in claim 1 wherein the organism accumulates in an aerobic atmosphere.

6. The method as recited in claim 1 wherein the pH is selected from between approximately 5 and 9.

7. The method as recited in claim 1 wherein the hydrolysate is contained in a first feedstock amount and wherein the method is made continuous with the addition of a second feedstock amount.

8. The method as recited in claim 7 wherein the second feedstock amount is added when succinic acid concentration is approximately 50 g/L.

9. A method of producing succinic acid from plant hyrdolysates comprising:
    a) supplying an organism from a genus of *Escherichia coli*, said organism containing mutations for the genes ptsG, pflB, and IdhA, wherein the mutations cause the organism to contain an inoperative phosphotransferase system, an inoperative pyruvate formate lyase system and an inoperative lactate dehydrogenase system;
    b) contacting said organism with said hydrolysate:
    c) allowing said organism to metabolize said hydrolysate; and
    d) isolating and recovering the succinic acid from the claimed organism.

10. The method as recited in claim 9 wherein the inoperative phosphotransferase system is the result of a point mutation.

11. The method as recited in claim 10 wherein the organism is AFP 404.

12. The method as recited in claim 9 wherein an inoperative phosphotransferase system, an inoperative pyruvate formate lyase system, and an inoperative iactate dehydrogenase system result from knockout mutations to the genes ptsG, pfIB, and IdhA.

13. The method as recited in claim 9 wherein the inoperative pyruvate formate lyase system results from a deletion mutation.

14. The method as recited in claim 9 wherein the inoperative lactate dehydrogenase system results from a knockout mutation.

15. The method as recited in claim 9 wherein the organism produces succinic acid from substrate contained in industrial-grade hydroysate in a ratio of between 0.6:1 and 1.3:1 succinic acid to substrate.

16. The method as recited in claim 15 wherein the organism is AFP 184.

17. The method as recited in claim 15 wherein the organism is capable of utilizing more than one substrate simultaneously to produce succinic acid simultaneously.

* * * * *

UNITED STATES PATENT AND TRADEMARK OFFICE
CERTIFICATE OF CORRECTION

PATENT NO. : 6,743,610 B2
DATED : June 1, 2004
INVENTOR(S) : Mark I. Donnelly, Cynthia Y. Sanville-Millard and Nhuan Phu Nghiem It is certified that error appears in the above-identified patent and that said Letters Patent is hereby corrected as shown below:

Column 10,
Line 25, after "hydrolysates" delete "said" and before "hydrolysates" insert -- said --.

Column 11,
Line 3, delete "iactate" and substitute therefor -- lactate --.

Signed and Sealed this

Fifteenth Day of March, 2005

JON W. DUDAS
*Director of the United States Patent and Trademark Office*